United States Patent
Buchtenirch

(10) Patent No.: US 6,835,252 B1
(45) Date of Patent: Dec. 28, 2004

(54) GOLD COLORED ALLOY USED FOR DENTISTRY AND JEWELRY

(76) Inventor: Martin Buchtenirch, 1 Sunny Slope Rd., Palos Park, IL (US) 60464-1550

( * ) Notice: Subject to any disclaimer, the term of this patent is extended or adjusted under 35 U.S.C. 154(b) by 0 days.

(21) Appl. No.: 10/828,957

(22) Filed: Apr. 21, 2004

(51) Int. Cl.⁷ .......................... C22C 30/00; C22C 29/00
(52) U.S. Cl. ...................... 148/442; 148/430; 420/580; 420/587
(58) Field of Search ................................ 148/442, 430; 420/580, 587

(56) References Cited

U.S. PATENT DOCUMENTS

| | | |
|---|---|---|
| 1,965,012 A | 7/1934 | Taylor |
| 3,424,577 A | 1/1969 | Nielson et al. |
| 3,767,391 A | 10/1973 | Tuccillo et al. |
| 3,925,066 A | 12/1975 | Kohrn et al. |
| 4,255,191 A | 3/1981 | Kropp |
| 4,264,359 A | 4/1981 | Harris et al. |
| 4,350,527 A | 9/1982 | Davitz |
| 4,370,164 A | 1/1983 | Harris et al. |
| 4,396,578 A | 8/1983 | Bales |
| 4,446,102 A | 5/1984 | Bales |
| 5,045,411 A * | 9/1991 | Taylor et al. ................ 428/672 |

* cited by examiner

*Primary Examiner*—Sikyin Ip
(74) *Attorney, Agent, or Firm*—Vedder Price Kaufman & Kammholz, P.C.

(57) ABSTRACT

A corrosive and tarnish resistant alloy comprising 13 to 25 percent by weight of gold, 20 to 36 percent by weight of silver, 23 to 32 percent by weight of copper, 16 to 25 percent by weight of zinc, and 1 to 4 percent by weight of silicate.

13 Claims, No Drawings

GOLD COLORED ALLOY USED FOR DENTISTRY AND JEWELRY

FIELD OF THE INVENTION

The invention relates generally to alloys, and specifically to alloys to make a gold colored alloy hard enough for jewelry and dentistry. In addition, this alloy should provide a material with the addition of silicate which does not easily tarnish.

Gold jewelry and utensils are valued because of their intrinsic worth and the gold color of the metal. For example, an alloy called astrolite™ was produced which comprises of silver, palladium, gold, and indium for commercial use, which is the subject of a U.S. Pat. No. 4,350,5427. However, a lower cost gold alloy is desirable.

BACKGROUND OF THE INVENTION

U.S. Pat. No. 5,134,039, Alexander, discloses a metal article comprising a metal selected by the group consisting of copper, silver and gold, another metal selected from the group consisting of zinc and a plurality of ultra fine particles having an average particle size of less than about 20 microns dispersed substantially evenly through said metal article. Wherein the ultra fine particles are water insoluble metal silicates. The invention is described as providing a process for the electrodeless plating of easily removable metals onto ultra fine usually inert particles.

U.S. Pat. No. 4,948,557, Davitz, discloses a gold-colored alloy for jewelry and dental purposes and the like consisting essentially of 24 to 27 percent palladium, 19 to 22 percent indium, 5 to 30 percent copper, 1 to 20 percent gold and the balance of silver. While gold, silver and copper are present, the additional constituents of palladium and indium teach away from the present invention, as does the absence of metal silicates.

U.S. Pat. No. 5,019,335, Davitz, discloses a gold-colored metal alloy consisting of 75 to 85 percent copper, 5 to 15 percent nickel, 0 to 12 percent indium and 0 to 12 percent zinc. It is also being indicated as being desirable to add approximately 0.01 percent iron and/or 0.05 percent silicon and to act as a grain refiner and fluidity enhancer, respectively. Thus, an alloy is disclosed that has a high copper content as well as zinc and silicon. However, nickel is present and indium may be present. Gold and/or silver are not present unlike the present invention.

U.S. Pat. No. 5,330,713, Davitz, discloses a gold-colored alloy which includes 6 to 20 percent by weight gold, 5 to 10 percent by weight indium, 5 to 12 percent by weight palladium, 23 to 40 percent by weight copper, 5 to 10 percent zinc and 23 to 40 percent silver. While gold, silver, copper and zinc are present, metal silicates are not present.

U.S. Pat. No. 3,925,066, Kohrn, et al., discloses a tarnish resistant Au/Ag alloy of low gold content exhibiting properties desired in jewelry manufacture consisting essentially of about 25 to 30 percent, by weight, gold, about 45 to 57 percent, by weight, silver, about 18 to 25 percent, by weight, of a metal selected from the group consisting of copper, nickel and mixtures thereof and 0 to about 5 percent by weight zinc.

U.S. Pat. No. 4,264,359, Harris, et al., discloses an alloy suitable for use in fabricating jewelry consisting essentially of about 25% by weight gold, about 11.75% to 12.60% by weight palladium, about 9.75% to 12.10% by weight silver, about 8.90 to 10.25% zinc, and about 0.045% to 0.065% by weight boron, balance copper.

U.S. Pat. No. 4,370,164, Harris, et al., discloses an alloy consisting essentially of 4% to 10% by weight gold, 54% to 61% by weight silver, 14% to 19% by weight copper, 4% to 7% by weight palladium, 9% to 14% by weight indium, 1% to 3% by weight zinc and 0.015% to 0.04% by weight boron.

U.S. Pat. No. 4,446,102, Bales, discloses the alloys comprising of 17–25% by weight gold, 10–27% by weight silver, 40–60% by weight copper, and 3–12% by weight zinc.

SUMMARY OF THE INVENTION

In accordance with this invention, an alloy is provided which contains Gold, Copper, Silicon, Silver and Zinc. This alloy will have a higher tarnish resistance and will be a harder alloy. In a 5% chlorine atmosphere, the present invention with silver is found to be superior to other low percentage of gold alloys; in fact has shown no discoloration. The corrosion resistance of this alloy is due to the addition of the silicate and gold.

An additional object of this invention is the production of an alloy mixed with gold and silver using zinc, a small amount of copper for hardness, and a small amount of silicate. This increases corrosion resistance and provides better working properties by reducing brittleness while still producing a low cost alloy.

Other objects of the present invention and advantages accruing therefrom, will be apparent to one who is skilled in the art from the following description. All percentages referred to are percent by weight, based on the total weight of material or mixture.

DETAILED DESCRIPTION OF THE PREFERRED EMBODIMENT

In a preferred embodiment, a corrosion resistant alloy is provided having 16 percent by weight of gold, 32.4 percent by weight of silver, 29 percent by weight of copper, 21 percent by weight of zinc and 1.6 percent by weight of silicate.

In another variant of the invention, the alloy consists essentially of 0.1% to 4 percent by weight silicon, 20 percent to 36 percent by weight of silver, 12 percent to 30 percent by weight zinc, 20 percent to 45 percent by weight copper and 13 percent to 25 percent by weight of gold.

To be useful in the manufacture of jewelry, an alloy must be malleable. The alloy cannot be brittle after casting and must retain its gold color while being used or being worn. A particularly preferred ratio is 16 percent by weight gold, 32.4 percent by weight silver, 21 percent by weight zinc, 29 percent by weight copper, 1.6 percent by weight of silicon. The zinc enhances the color and provides increased tarnish and corrosion resistance, the silicon acts as a de-oxidizer as well as prevents any tarnish and copper acts as a hardener and enhances color.

| IDEAL FORMULA FOR MARALLOY | | |
|---|---|---|
| Gold | 16% | ±5% |
| Silver | 32.4% | ±5% |
| Copper | 29% | ±5% |
| Zinc | 21% | ±5% |
| Silicate | 1.6% | ±5% |

In accordance with this invention, a gold colored, corrosive resistant alloy is provided which consists of the following, 13 to 25 percent by weight of gold, 20 to 36 percent by weight of silver, 23 to 32 percent by eight of copper, 6 to 25 percent by weight of zinc, and 1 to 4 percent by weight of silicate.

The alloys described herein due to their corrosion resistance, malleability and resistance to fracture are also highly desirable for use in dental applications such as fillings, bridges and implants.

PHYSICAL PROPERTIES OF THIS ALLOY

The silicate and the gold of the present alloy prevent the tarnishing of the alloy. The gold and copper help give the alloy the desired gold color. The copper hardens the alloy as well as adds to the color of the alloy. The zinc helps in deoxidizing of the alloy and gives the color a lighter yellow color. The silicate helps in keeping the alloy from tarnishing.

This alloy in a 20% chlorine atmosphere is found to be equivalent to 10 karat gold. This alloy can therefore be used for clasps on rings, and all sorts of jewelry. It can be rolled and stamped as well as cast.

The above has been offered for illustrated purposes and is not intended to limit the invention of the application, which is defined in the claims below.

What is claimed is:

1. A corrosive and tarnish resistant alloy consisting essentially of 13 and 25 percent by weight of gold, 20 to 36 percent by weight of silver, 23 to 32 percent by weight of copper, 16 to 25 percent by weight of zinc, and 1 to 4 percent by weight of silicate.

2. The alloy according to claim 1 having a casting temperature of 1785 to 1825 degrees Fahrenheit.

3. The alloy according to claim 1 melts having a temperature of approximately 1375 degrees Fahrenheit.

4. The alloy according to claim 1 and further comprising copper-silicate.

5. The alloy according to claim 1 and having a specific gravity of 8.567 g./cc. ±0.75 g./cc.

6. The alloy according to claim 1 and having gold and said copper silicate provide enhanced tarnish resistance.

7. The alloy according to claim 1 wherein said zinc is used to lighten the color of alloy and to act as a scavenger.

8. Alloy for the manufacture of jewelry comprising, by weight:

| | | |
|---|---|---|
| Gold | 16% | ±5% |
| Silver | 32.4% | ±5% |
| Copper | 29% | ±5% |
| Zinc | 21% | ±5% |
| silicate | 1.6% | ±5% |

9. The alloy according to claim 8 and having a Brinell hardness of 160 bench cooled and 140 quenched, ±5%.

10. An improved dental alloy comprising a corrosive and tarnish resistant alloy consisting essentially of 13 to 25 percent by weight of gold, 20 to 36 percent by weight of silver, 22 to 32 percent by weight of copper, 16 to 25 percent by weight of zinc, and 1 to 4 percent by weight of silicate.

11. A corrosive and tarnish resistant alloy comprising 13 to 25 percent by weight of gold, 20 to 36 percent by weight to silver, 23 to 32 percent by weight of copper, 16 to 25 percent by weight of zinc, and 1 to 4 percent by weight of silicate.

12. A dental alloy suitable for crown, bridges, and other dental apparatus comprising of a gold colored, a corrosive and tarnish resistant alloy consisting essentially of 13 to 25 percent by weight of gold, 20 to 36 percent by weight of silver, 23 to 32 percent by weight of copper, 16 to 25 percent by weight of zinc, and 1 to 4 percent by weight of silicate.

13. A corrosive and tarnish resistant alloy comprising 13 to 25 percent by weight of gold, 20 to 36 percent by weight of silver, 23 to 32 percent by weight of copper, 16 to 25 percent by weight of zinc, and 1 to 4 percent by weight of silicate.

* * * * *